(12) United States Patent
Wong

(10) Patent No.: US 9,358,225 B2
(45) Date of Patent: Jun. 7, 2016

(54) METHOD FOR TREATING NEURODEGENERATION USING A P38MAPK INHIBITOR

(71) Applicant: Bach Pharma, Inc., North Andover, MA (US)

(72) Inventor: Paul K. Y. Wong, Smithville, TX (US)

(73) Assignee: Bach Pharma, Inc., North Andover, MA (US)

( * ) Notice: Subject to any disclaimer, the term of this patent is extended or adjusted under 35 U.S.C. 154(b) by 0 days.

(21) Appl. No.: 14/215,889

(22) Filed: Mar. 17, 2014

(65) Prior Publication Data

US 2014/0303212 A1    Oct. 9, 2014

Related U.S. Application Data

(60) Provisional application No. 61/790,027, filed on Mar. 15, 2013.

(51) Int. Cl.
| | | |
|---|---|---|
| *A61K 31/10* | (2006.01) | |
| *A61K 31/4184* | (2006.01) | |
| *A61K 31/4188* | (2006.01) | |
| *A61K 31/44* | (2006.01) | |
| *A61K 31/4439* | (2006.01) | |

(52) U.S. Cl.
CPC ............. *A61K 31/4439* (2013.01); *A61K 31/10* (2013.01); *A61K 31/4184* (2013.01); *A61K 31/4188* (2013.01); *A61K 31/44* (2013.01)

(58) Field of Classification Search
CPC .............. A61K 31/10; A61K 31/4184; A61K 31/4188; A61K 31/44
See application file for complete search history.

(56) References Cited

U.S. PATENT DOCUMENTS

| | | | | |
|---|---|---|---|---|
| 6,288,089 | B1 * | 9/2001 | Zawada et al. | 514/341 |
| 6,645,989 | B2 * | 11/2003 | Adams et al. | 514/341 |
| 7,998,507 | B2 * | 8/2011 | Bosch et al. | 424/489 |
| 2005/0090474 | A1 * | 4/2005 | Naor | 514/170 |
| 2011/0172206 | A1 | 7/2011 | Zack et al. | |

* cited by examiner

*Primary Examiner* — Yong Chong
(74) *Attorney, Agent, or Firm* — Occhiuti & Rohlicek LLP

(57) ABSTRACT

Ataxia-telangiectasia (A-T) is a progressive degenerative disorder that results in major neurological disability. In A-T patients, necropsy has revealed atrophy of all cerebellar cortical layers with extensive Purkinje and granular cell loss. We have previously identified an increase in phospho-p38MAPK levels, which was accompanied by downregulation of Bmi-1 and upregulation of p21, as key components of the mechanism causing defective proliferation of neural stem cells (NSCs) isolated from subventricular zone (SVZ) of Atm-null mice. Our results demonstrate that restoration of NSCs by pharmacologic inhibition of p38MAPK signaling has the potential to treat neurological defects of A-T. This study provides new insights into the therapeutic strategy targeting NSCs rather than replacing impaired neurons not only for A-T, but for other neurodegenerative disorders as well.

1 Claim, 9 Drawing Sheets

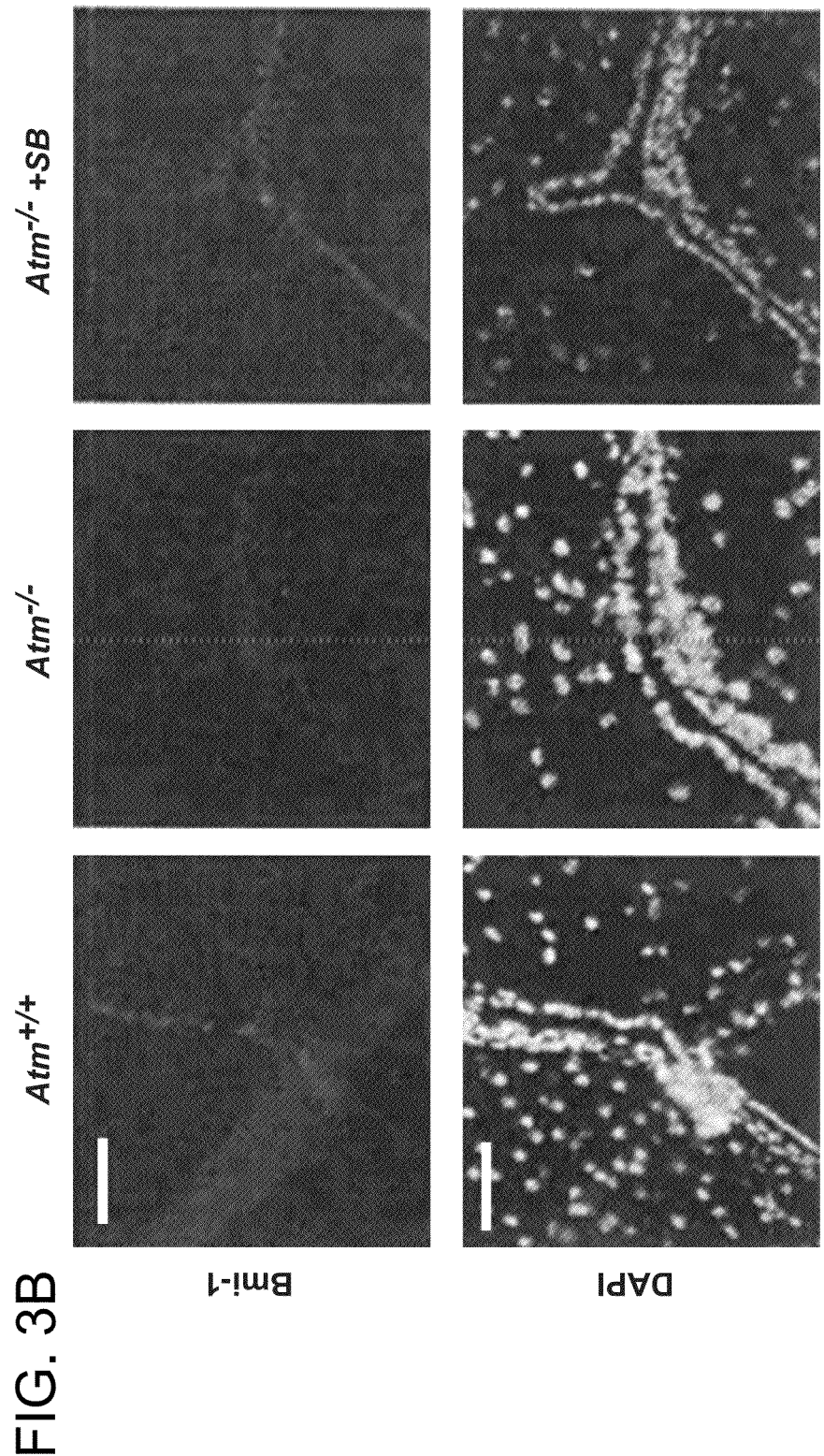

A

B

C

D

E

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agaatcccac ctgcagtcat ctc                                            23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccttccagg taaccacttc cg                                             22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 3
agaaaccagc ctggacacca aatc                                          24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accacgatgt tcctcttgag gtg                                           23
```

METHOD FOR TREATING NEURODEGENERATION USING A P38MAPK INHIBITOR

SEQUENCE LISTING

The instant application contains a Sequence Listing which has been submitted electronically in ASCII format and is hereby incorporated by reference in its entirety. Said ASCII copy, created on Jun. 23, 2014, is named 117735-02202_SL.txt and is 1,218 bytes in size.

INTRODUCTION

A-T (ataxia-telangiectasia) is a genetic disease in which the Atm (A-T mutated) gene is mutated. The predominant neurological abnormalities in A-T are characterized by progressive neurodegeneration primarily resulting from loss of cerebellar Purkinje cells. With time, however, other regions of the brain are also affected (Boder, 1985; Sardanelli et al., 1995). In $Atm_{-/-}$ mice, degeneration of different types of neurons including Purkinje cells in cerebellum and dopaminergic neurons in substantia nigra has been reported (Barlow et al., 1996; Kuljis et al., 1997; Eilam et al., 1998, 2003). These phenotypes are similar to those in patients with A-T, indicating that $Atm_{-/-}$ mice are a useful model to study the mechanisms of A-T neurodegeneration. Therefore, we have used $Atm_{-/-}$ mice to identify potential targets that contribute to the neuropathology of A-T and to develop therapeutic treatments for A-T.

During the normal neurogenesis, ATM expression is abundant in neural stem cells (NSCs) but is markedly reduced as they differentiate (Allen et al., 2001), suggesting that ATM plays a role in neurogenesis. The subventricular zone (SVZ) adjacent to the lateral ventricle is the largest niche for the neurogenesis in the adult mammalian brain (Quinones-Hinojosa and Chaichana, 2007). Although a substantial alteration of the SVZ tissue was reported depending on the type of disorder (Curtis et al., 2007; Oizumi et al., 2008), alteration of the SVZ in A-T disease has remained unexplored. NSCs are defined by their ability to self-renew, differentiate into cells of glial and neuronal lineages, and to respond to developmental cues to populate or replace degenerating neurons in the central nervous system (CNS) (Flax et al., 1998). For this reason, proper control of NSC self-renewal and differentiation is crucial for the maintenance of neural homeostasis and in determining the number of neuronal cells in the brain (Gage, 2000).

We have previously reported that p38MAPK (hereafter p38) was activated in $Atm_{-/-}$ NSCs, which results in defective proliferation and self-renewal. This was accompanied by altered levels of p21 and the polycomb protein Bmi-1. However, treatment with a specific p38 inhibitor SB203580 (4-[5-(4-Fluorophenyl)-2-[4-(methylsulphonyl)phenyl]-1H-imidazol-4-yl]pyridine) restored normal levels of p21 and Bmi-1 as well as normal proliferation in cultured $Atm_{-/-}$ NSCs (Kim and Wong, 2009a; Kim et al., 2011).

At present, there is no therapy available to cure or prevent A-T neurodegeneration. In this study we investigated the feasibility of an in vivo therapeutic strategy by targeting p38 signaling to restore defects in $Atm_{-/-}$ NSCs, thereby preventing A-T neurodegeneration. Our data showed that SB203580 (4-[5-(4-Fluorophenyl)-2-[4-(methylsulphonyl)phenyl]-1H-imidazol-4-yl]pyridine) restored normal levels of Bmi-1 and p21 and rescued NSCs in $Atm_{-/-}$ SVZ. We also demonstrated that rescuing $Atm_{-/-}$ NSCs via restoring molecular homeostasis not only mediated functional recovery, but increased the number of Purkinje cells in the cerebellum. It is likely that NSCs could repopulate damaged sites in the $Atm_{-/-}$ mouse brain by shifting the differentiation fate of their progeny to compensate for the degenerated neurons. This study provides new insights into the therapeutic strategy targeting NSCs rather than replacing impaired neurons for A-T and other neurodegenerative disorders.

Materials and Methods

Animals

The $Atm_{-/-}$ mice were originally generated by Dr. C. Barlow (Barlow et al., 1996). They were purchased from the Jackson Laboratory (Bar Harbor, Me.). Offspring of $Atm_{+/-}$ breeders were genotyped using real-time polymerase chain reaction-based assays of mouse tail DNA. Atm mice (1-month old) were divided into 3 groups: PBS-treated $Atm_{+/+}$ mice (n=10/group); PBS-treated $Atm_{-/-}$ mice (n=9/group); and SB203580 (4-[5-(4-Fluorophenyl)-2-[4-(methylsulphonyl)phenyl]-1H-imidazol-4-yl]pyridine) treated $Atm_{-/-}$ mice (n=10/group). Mice were intraperitoneally injected with either PBS or SB203580 (4-[5-(4-Fluorophenyl)-2-[4-(methylsulphonyl)phenyl]-1H-imidazol-4-yl]pyridine) (5 mg/kg body weight) at 2-day intervals for 2 months. Animals were sacrificed one day after the last administration. Animal care was in accordance with The University of Texas MD Anderson Cancer Center guidelines for animal experiments.

Histological Analysis of Cerebellum and SVZ by Immunofluorescence Staining

Mice (P90) were anesthetized and perfused through the heart with 4% paraformaldehyde. Brains were dissected out, postfixed in the same fixative, and cryoprotected in 30% sucrose at 4° C. Cerebellar coronal cryostat sections (7 μm thick) were stained with hematoxylin/eosin (H&E) for cerebellar and for SVZ histology. Tissue sections were incubated in blocking solution consisting of 3% fetal bovine serum and 0.1% Triton X-100 in PBS at room temperature for 30 min and then reacted with specific primary antibodies at 4° C. overnight. Each sample was washed with PBS three times, for 10 min each, and then stained by secondary antibodies for 1 hour. Finally, each sample was sealed with mounting medium containing 4',6-diamidino-2-phenylindole (DAPI) to stain cell nuclei and was visualized by fluorescence microscopy (Olympus IX2-SL).

Primary antibodies for detection of neuronal cells include nestin (Santa Cruz Biotechnology) and vimentin (Sigma-Aldrich) for undifferentiated neural progenitors, calbindin-D-28K (Sigma-Aldrich) specific for Purkinje cells, microtubule-associated protein 2 (MAP2, Cell Signaling Technology) for dendritic trees of neurons, glial fibrillary acidic protein (GFAP; Santa Cruz Biotechnology) for astrocytes, myelin 2',3'-cyclic nucleotide 3'-phosphodiesterase (CNPase; Millipore) for oligodendrocytes. Secondary antibodies include goat anti-mouse or anti-rabbit IgG and donkey anti-goat IgG (Jackson ImmunoResearch) conjugated with a fluorescent dye (FITC or Texas Red).

Protein Analysis

For protein measurement, cells in 10-cm dishes were collected and washed once with ice-cold PBS and then resuspended into lysis buffer containing 150 mM NaCl, 0.5% w/v sodium dodecyl sulfate (SDS), 0.5% v/v NP-40, 0.5% w/v sodium deoxycholate, 1 mM EGTA, and a mixture of protease inhibitors (Complete Mini tablets; Boehringer Mannheim). For Western blotting, protein concentrations were determined using a Bradford reagent (BioRad). Proteins (30 μg) were separated by SDS-polyacrylamide gel electrophoresis on 10% gels, and transferred to polyvinylidene difluoride membranes prior to incubation with primary antibodies.

β-actin served as a control protein on the same blot to eliminate loading variations. Antibodies used for western blotting analysis were anti-calbindin-D-28K and anti-vimentin (Sigma-Aldrich); anti-phospho-p38 (Th180/Tyr182), anti-p38, and anti-Map2 (Cell Signaling Technology); anti-nestin, anti-GFAP, anti-p21 and anti-β-actin (Santa Cruz Biotechnology); anti-CNPase and anti-Bmi-1 (Millipore).

Quantitative Reverse transcription-PCR

Expression levels for bmi-1, p21Cip1, Calbindin-K, and gfap were quantified, relative to gapdh, internal RNA control, by quantitative RT-PCR (qRT-PCR). Sequences of PCR primers are listed as follows.

```
Primers that amplified bmi-1 were Mm03053308_g1.

Primers that amplified p21Cip1:
cdkn1a (p21) were Mm00432448_m1.

Primers that amplified Calbindin-K were sense,
                                      (SEQ ID NO: 1)
5'-AGAATCCCACCTGCAGTCATCTC-3'
and antisense,
                                      (SEQ ID NO: 2)
5'-TCCTTCCAGGTAACCACTTCCG-3'.

Primers that amplified gfap were sense,
                                      (SEQ ID NO: 3)
5'-AGAAACCAGCCTGGACACCAAATC-3'
and antisense,
                                      (SEQ ID NO: 4)
5'-ACCACGATGTTCCTCTTGAGGTG-3'.
```

Differentiation of Neural Stem Cells

Neurospheres were obtained from the SVZ of P1 pup, and were maintained in culture essentially as reported (Kim and Wong, 2009a). Neurospheres were enzymatically dissociated as described above. The cells were seeded onto chamber slides, and then maintained in medium containing 10% FBS without EGF for 7 days. Antibodies used for characterization of differentiated cells were anti-Map2 (Cell Signaling Technology) and anti-GFAP (Santa Cruz Biotechnology).

Behavioral Test

We have devised a modified version of the standardized rotarod protocol (Columbus Instruments, Columbus, Ohio). After treatment, prior to the test, $Atm_{+/+}$ and $Atm_{-/-}$ mice had training on a modified rotarod test for 3 days. Three trials per day for 3 days were carried out to sustain mice on a rotating rod at 25 rpm. The apparatus contains a circular metal rod with a cross-sectional diameter of 0.7 cm with scratches to provide a sufficiently nonslip surface. The rod was suspended at a height of 16 cm. Following training, three trials of mouse motor coordination were assessed by measuring the time before falling off the rotarod moving at 25 rpm.

Statistic Analysis

Each experiment, including behavioral test, body weight measure and qRT-PCR was repeated at least three times. The proportion of mRNA expression was analyzed from a series of tissue sections. Results were presented as the means±SD, and differences were considered significant at $p<0.05$. Statistical comparisons of values for $Atm_{+/+}$ mice vs. $Atm_{-/-}$ mice, and for PBS-treated mice vs. SB203580 (4-[5-(4-Fluorophenyl)-2-[4-(methylsulphonyl)phenyl]-1H-imidazol-4-yl]pyridine) treated mice were made using an analysis of variance (ANOVA), followed by Bonferroni's post hoc test.

Results

NSC Depletion and Abnormal Signaling in the SVZ of $Atm_{-/-}$ Mice

We have previously reported that in the absence of ATM, cultured NSCs from the SVZ of $Atm_{-/-}$ mice displayed defective proliferation and self-renewal. We have also shown that $Atm_{-/-}$ NSCs had lower levels of Bmi-1, yet also demonstrated higher levels of p21 (Kim and Wong, 2009a; Kim et al., 2011). To investigate whether results from in vitro culture recapitulate in vivo microenvironments of $Atm_{-/-}$ mice, we examined SVZ cytoarchitecture of adult (P90) $Atm_{+/+}$ (n=4) and $Atm_{-/-}$ mice (n=4). The wall architecture of the lateral ventricle of $Atm_{-/-}$ mice was found to be normal (FIG. 1A upper panel).

However, they showed a marked decrease in the NSC-specific protein marker vimentin levels in the wall of the lateral ventricular layer as compared to $Atm_{+/+}$ controls, indicating a depletion of vimentin-positive NSCs (FIG. 1A lower panel). Consistent with our in vitro study of defective proliferation and self-renewal in $Atm_{-/-}$ NSCs as described above (Kim and Wong, 2009a), this is the first in vivo evidence, showing that in the absence of ATM, NSC population is abnormally depleted in SVZ tissue.

We next compared in vivo levels of Bmi-1 and p21 in the SVZ of $Atm_{+/+}$ and $Atm_{-/-}$ mice. Immunohistochemical analysis revealed markedly decreased Bmi-1 and increased p21 levels in the $Atm_{-/-}$ mouse SVZ (FIG. 1B), which was also consistent with our in vitro results from the $Atm_{-/-}$ NSCs (Kim and Wong, 2009a; Kim et al., 2011). Similar to the reduced levels of vimentin in $Atm_{-/-}$ SVZ as shown in FIG. 1A, another NSC-selective marker, nestin, was significantly reduced by >90% loss in $Atm_{-/-}$ SVZ compared to $Atm_{+/+}$ SVZ (FIG. 1C). Since Bmi-1 has been implicated as an essential molecule for NSC proliferation, our findings also correlate lower levels of Bmi-1 with NSC depletion in the $Atm_{-/-}$ mouse SVZ.

p38 Activation Contributes to NSC Depletion in $Atm_{-/-}$ SVZ

We have previously demonstrated that $Atm_{-/-}$ NSCs showed elevated levels of ROS and that the activation of p38 signaling in response to elevated ROS levels resulted in defective self-renewal and proliferation in cultured NSCs (Kim and Wong, 2009a). We therefore asked whether ATM deficiency alters the activation status of p38 in SVZ in vivo and whether altered p38 signaling may result in NSC loss in $Atm_{-/-}$ SVZ. Immunofluorescence staining revealed increased levels of phospho-p38 in $Atm_{-/-}$ SVZ compared with in $Atm_{+/+}$ SVZ (FIG. 2A). This p38 activation was also evident in $Atm_{-/-}$ SVZ tissue by western blot analysis using antibody against phospho-p38 (FIG. 2B). Based on these results, we hypothesized that treatment with pharmacologic inhibition of the p38 signaling should restore the NSC proliferation and self-renewal, which may promote NSC survival in $Atm_{-/-}$ SVZ. In an attempt to test our hypothesis, we treated 1-month-old $Atm_{-/-}$ mice with p38 specific inhibitor SB203580 (4-[5-(4-Fluorophenyl)-2-[4-(methylsulphonyl)phenyl]-1H-imidazol-4-yl]pyridine) for 2 months, and then compared the levels of nestin in the SVZ with PBS-treated $Atm_{-/-}$ mice. We observed that nestin levels were significantly reduced in the SVZ of PBS-treated $Atm_{-/-}$ mice (hereafter $Atm_{-/-}$) compared with PBS-treated $Atm_{+/+}$ controls (hereafter $Atm_{+/+}$), but improved in the SVZ of SB203580 (4-[5-(4-Fluorophenyl)-2-[4-(methylsulphonyl)phenyl]-1H-imidazol-4-yl]pyridine) treated $Atm_{-/-}$ mice (hereafter $Atm_{-/-}$+SB) (FIG. 2C). However, SB203580 (4-[5-(4-Fluorophenyl)-2-[4-(methylsulphonyl)phenyl]-1H-imidazol-4-yl]pyridine) did not fully recover nestin expression to levels in $Atm_{+/+}$ SVZ, indicating that p38 activation may be only partially responsible for NSC depletion in $Atm_{-/-}$ SVZ in vivo context.

Restoration of NSCs in $Atm_{-/-}$ SVZ Via Inhibition of p38 Signaling

We investigated the mechanism by which p38 signaling plays a role in NSC depletion in $Atm_{-/-}$ SVZ and whether inhibition of p38 could reverse this mechanism. Mice were treated with a p38 inhibitor SB203580 (4-[5-(4-Fluorophenyl)-2-[4-(methylsulphonyl)phenyl]-1H-imidazol-4-yl]pyridine) as mentioned above, and then effects of the treatment on signaling molecules including Bmi-1 and p21 along with vimentin were analyzed. Indeed, SB203580 (4-[5-(4-Fluorophenyl)-2-[4-(methylsulphonyl)phenyl]-1H-imidazol-4-yl]pyridine) treatment resulted in an increase in nestin-positive cells in $Atm_{-/-}$ SVZ (FIG. 1C and FIG. 2C). In accordance with this result, SB203580 (4-[5-(4-Fluorophenyl)-2-[4-(methylsulphonyl)phenyl]-1H-imidazol-4-yl]pyridine) restored the levels of another NSC marker, vimentin, in $Atm_{-/-}$ SVZ (FIG. 3A upper panel). Since inhibition of p38 increased vimentin-positive NSCs in the SVZ, SB203580 should theoretically increase the levels of NSC proliferation-promoting protein Bmi-1. As expected, Bmi-1 levels were greatly restored in SB203580 (4-[5-(4-Fluorophenyl)-2-[4-(methylsulphonyl)phenyl]-1H-imidazol-4-yl]pyridine) treated $Atm_{-/-}$ SVZ (FIG. 3A middle panel). We also observed that SB203580 (4-[5-(4-Fluorophenyl)-2-[4-(methylsulphonyl)phenyl]-1H-imidazol-4-yl]pyridine) reduced p21 levels in $Atm_{-/-}$ SVZ (FIG. 3A lower panel).

Immunofluorescence staining using anti-Bmi-1 antibody further confirmed that ATM deficiency resulted in >80% reduction in Bmi-1 intensity. The SB203580 (4-[5-(4-Fluorophenyl)-2-[4-(methylsulphonyl)phenyl]-1H-imidazol-4-yl]pyridine) treatment restored Bmi-1 to normal levels (FIG. 3B), as evidenced by western blot analysis (FIG. 3C). Quantitative RT-PCR analysis revealed that mRNA expression of bmi-1 remained unaffected (FIG. 3D), although Bmi-1 protein levels were greatly reduced in $Atm_{-/-}$ SVZ (FIG. 3A, 3B, 3C). This result is consistent with our previous reported data that Bmi-1 expression level is regulated by a post-transcriptional mechanism in $Atm_{-/-}$ NSCs (Kim et al., 2011). By contrast, p21 mRNA expression was decreased by SB203580 (4-[5-(4-Fluorophenyl)-2-[4-(methylsulphonyl)phenyl]-1H-imidazol-4-yl]pyridine), confirming that inhibition of p38 restores Bmi-1 protein levels in $Atm_{-/-}$ SVZ, which suppresses expression of p21 (FIG. 3D). These results provide strong evidence that p38 signaling suppresses NSC survival and proliferation through downregulation of Bmi-1 in $Atm_{-/-}$ SVZ.

SB203580 Treatment Improves $Atm_{-/-}$ Cerebellar Purkinje Cells

ATM deficiency affects the cerebellum, leading to poor coordination in A-T patients (Boder, 1985; Boder and Sedgwick, 1958). Therefore, we investigated whether the cerebellum exhibits atrophy in $Atm_{-/-}$ mice. Cerebella in both $Atm_{+/+}$ and $Atm_{-/-}$ mice had a tri-laminar architecture with intact molecular layer (ML), Purkinje neuron layer (PN), and granule cell layers (GL). However, $Atm_{-/-}$ cerebellum showed altered distribution of Purkinje cells in the PN layer when compared to $Atm_{+/+}$ control (FIG. 4A upper panel), which is consistent with previous studies (Boder, 1985; Sardanelli et al., 1995). To examine the distribution and the number of the Purkinje cells, cerebellar Purkinje cells were stained immunohistochemically with the selective protein marker calbindin. In addition to altered cytoarchitecture at the PN layer, the number of these cells decreased by 30% in $Atm_{-/-}$ mouse cerebellum (FIG. 4A lower panel and FIG. 4B). Decrease in calbindin (calb) protein and calbindin mRNA expression in $Atm_{-/-}$ cerebellum tissue further confirmed Purkinje cell loss in $Atm_{-/-}$ cerebellum (FIG. 4C and FIG. 4D). In contrast, expression of the apoptotic marker Bax in adult $Atm_{-/-}$ cerebellum was not changed in western blot analysis (FIG. 4C). These results indicate that Purkinje cell loss in $Atm_{-/-}$ cerebellum is likely triggered by a molecular mechanism independent of Bax-mediated apoptosis. Our observations further indicate that the $Atm_{-/-}$ mice used for the present study recapitulate neuropathological phenotypes of A-T patients as a useful model to elucidate the mechanisms underlying neurodegeneration and to test strategies for the treatment of A-T disease. Based on the results we observed in $Atm_{-/-}$ cerebellum, we treated young (p30) $Atm_{-/-}$ mice with a p38 specific inhibitor SB203580 (4-[5-(4-Fluorophenyl)-2-[4-(methylsulphonyl)phenyl]-1H-imidazol-4-yl]pyridine) and investigated the effects of treatment on cerebellar Purkinje cells in adult (P90) $Atm_{-/-}$ mice. We found that the number of Purkinje cells was restored to normal by SB203580 (4-[5-(4-Fluorophenyl)-2-[4-(methylsulphonyl)phenyl]-1H-imidazol-4-yl]pyridine) treatment (FIG. 4A and FIG. 4B). Analysis of calb protein and mRNA expression of calbindin also confirmed restoration of Purkinje cells in $Atm_{-/-}$ cerebellum by SB203580 (4-[5-(4-Fluorophenyl)-2-[4-(methylsulphonyl)phenyl]-1H-imidazol-4-yl]pyridine) treatment (FIG. 4C and FIG. 4D).

To further examine whether the reduced number and morphological alterations observed in $Atm_{-/-}$ cerebellum is correlated to reduced dendritic trees in $Atm_{-/-}$ mice, we performed immunohistochemical analysis of the distribution of microtubule-associated protein 2 (MAP2) in the cerebellum of $Atm_{+/+}$ and $Atm_{-/-}$ mice. All regions examined showed a pattern of intense MAP2 staining in dendrites and a weaker staining in cell bodies. In the molecular layer of the cerebellar cortex, MAP2 expression was found intensively throughout distal Purkinje cell dendrites, yet was only sparsely observed in Purkinje cell bodies and proximal dendrites (FIG. 4E). Immunostaining data revealed a dendritic network both in $Atm_{+/+}$ and $Atm_{-/-}$ cerebellum, suggesting that in the absence of ATM, Purkinje cell dendrites continue to develop normally and that Purkinje cell loss observed in $Atm_{-/-}$ cerebellum did not result in morphological differences in dendritic trees.

Abnormal Differentiation in $Atm_{-/-}$ NSCs

Previous studies demonstrated that normal p38 signaling is essential for NSC differentiation (Androutsellis-Theotokis et al., 2006). Bmi-1 is also important for maintenance of NSC multipotency, which is required for generating neurons (Fasano et al., 2007, 2009). We showed here that $Atm_{-/-}$ SVZ tissue have abnormal activation of p38 and decreased Bmi-1 levels, compared to $Atm_{+/+}$ SVZ tissue (FIG. 2A). Therefore, we hypothesized that abnormal p38-Bmi-1 signaling in $Atm_{-/-}$ NSCs may affect their neurogenic capacity, which would change the fate of the progenitor cells.

To verify our hypothesis, NSCs were isolated from SVZ tissue of newborn pups, and were maintained in medium containing 10% FBS, without EGF, for 7 days, and then their differentiating phenotypes were studied. We observed that although $Atm_{-/-}$ NSCs are capable of undergoing multilineage differentiation, these NSCs showed abnormal differentiation, evidenced by different compositions of differentiated GFAP-positive astrocyte and Map2-positive neuron in culture (FIG. 5). Since we showed that p38 is constitutively activated in $Atm_{-/-}$ SVZ (FIG. 2), this result is consistent with a previous study reporting that p38 activation results in abnormal differentiation in $NPC1_{-/-}$ (The Niemann-Pick type C1) NSCs (Yang et al., 2006). Perhaps the NSC status in $Atm_{-/-}$ SVZ represents the defective self-renewal and survival (FIG. 1 concomitant with increased and altered differentiation events.

Abnormal Differentiation in $Atm_{-/-}$ NSCs can be Restored by SB203580 Treatment The effects of p38 inhibition on the neurogenic capacity of NSCs in $Atm_{-/-}$ mice were investigated. As shown, tissue obtained from $Atm_{-/-}$ mice showed abnormal morphology and reduced numbers of Purkinje cells in the cerebellum, but which was recovered by SB203580 (4-[5-(4-Fluorophenyl)-2-[4-(methylsulphonyl)phenyl]-1H-imidazol-4-yl]pyridine) treatment (FIG. 6 upper panel). Immunohistochemical analysis also revealed that $Atm_{-/-}$ astrocytes in the cerebellum cortex have normal cell bodies in the Purkinje neuron layer and extend into the molecular layer. However, these cells were presented at slightly lower numbers in $Atm_{-/-}$ cerebellar cortex compared to $Atm_{+/+}$ controls. SB203580 (4-[5-(4-Fluorophenyl)-2-[4-(methylsulphonyl)phenyl]-1H-imidazol-4-yl]pyridine) treatment resulted in improved numbers of astrocytes in $Atm_{-/-}$ cerebellar cortex (FIG. 6 middle panel). This is consistent with our previous report that $Atm_{-/-}$ astrocytes showed decreased proliferation (Kim and Wong, 2009b). We also analyzed the oligodendrocytes in $Atm_{-/-}$ cerebellar cortex based on immunostaining using antibodies against 2,3-cyclic nucleotide 3-phosphohydrolase (CNPase), a myeline specific enzyme. The localization of CNPase-positive oligodendrocytes within the cerebellar cortex was determined to be within the granule cell layer and extended from the white matter tracts through the Purkinje neuron layer to the molecular layer. The extension of CNPase-positive oligodendrocytes in $Atm_{-/-}$ mice was less developed than in $Atm_{+/+}$ mice. However, SB203580 (4-[5-(4-Fluorophenyl)-2-[4-(methylsulphonyl)phenyl]-1H-imidazol-4-yl]pyridine) treatment promoted this extension (FIG. 6 lower panel). These results demonstrate that ATM plays a role in neuronal cell differentiation through p38 signaling and that abnormal neuronal cells in $Atm_{-/-}$ mice cerebellum may result from the impairment of normal differentiation of NSCs.

SB203580 Treatment Recovers Neuromotor Function of $Atm_{-/-}$ Mice

Although neuromotor deficits in $Atm_{-/-}$ mice do not reach the level of severity observed in A-T humans, histopathological evidence of altered SVZ and cerebellum is present in $Atm_{-/-}$ -mice (FIG. 1, 4). Using our rotorod motor skill test outlined in our methods allowed us to measure how long the mice can stay upright on the rotating rod and assess the functional recovery of motor behavior mediated by SB203580 (4-[5-(4-Fluorophenyl)-2-[4-(methylsulphonyl)phenyl]-1H-imidazol-4-yl]pyridine) treatment. Prior to the test, all mice had training of the rotarod test for 3 days and they showed a stable learning of performance, as evidenced by an increase in the duration time on the rotarod. We found that our rotarod test reveals clear neuromotor differences between 3 month-old $Atm_{-/-}$ vs. $Atm_{+/+}$ mice, and that $Atm_{-/-}$ mice treated with antioxidant 5-carboxy-1,1,3,3-tetramethyl-isoindolin-2-yloxyl (CTMIO) and N-acetyl-L-cysteine (NAC) stayed on the rod as long as did $Atm_{+/+}$ mice (data not shown). These results are consistent with previous reporting in other studies with $Atm_{-/-}$ mice (Browne et al., 2004; Gueven et al., 2006) and verified that our testing protocol can be used to test neuromotor function in $Atm_{-/-}$ mice. Throughout the study, $Atm_{+/+}$ mice consistently maintained balance on the rotarod for the mean latency of 75 sec. Conversely, $Atm_{-/-}$ mice displayed significant motor impairment when compared to $Atm_{+/+}$ control mice. This test disclosed clear neuromotor differences between $Atm_{+/+}$ vs. $Atm_{-/-}$ mice at 3 months of age, indicating that $Atm_{-/-}$ mice develop a movement disorder similar to ataxia in A-T humans. On the other hand, SB203580 (4-[5-(4-Fluorophenyl)-2-[4-(methylsulphonyl)phenyl]-1H-imidazol-4-yl]pyridine) treated mice performed significantly better on the rotarod than did the $Atm_{-/-}$ groups, although they did not fully perform to the levels of the $Atm_{+/+}$ group (FIG. 7A). Body weight measurements following the behavioral testing Showed that $Atm_{-/-}$ mice displayed significant weight loss compared to the $Atm_{+/+}$ mice, but SB203580 (4-[5-(4-Fluorophenyl)-2-[4-(methylsulphonyl)phenyl]-1H-imidazol-4-yl]pyridine) treated $Atm_{-/-}$ mice improved their body weight close to normal (FIG. 7B). In contrast, $Atm_{+/+}$ mice treated with SB203580 (4-[5-(4-Fluorophenyl)-2-[4-(methylsulphonyl)phenyl]-1H-imidazol-4-yl]pyridine) did not differ from their PBS-treated control group (data not shown), demonstrating no stressful nature of treatment. The data suggests that SB203580 (4-[5-(4-Fluorophenyl)-2-[4-(methylsulphonyl)phenyl]-1H-imidazol-4-yl]pyridine) treatment has therapeutic effects that correct neuromotor deficits in $Atm_{-/-}$ mice.

Discussion

In the normal brain, control of the fate of NSCs involving self-renewal, differentiation, and death is critical in determining the number of neuronal cells in the brain (Quinones-Hinojosa and Chaichana, 2007). Thus, in recent years an increasing amount of work on NSCs has been carried out and progress has been made in elucidating signaling pathways and factors that control the NSC fate. Much remains to be uncovered regarding disease-related changes in the NSC population in the brain. Once these changes are identified, an appropriate strategy could be developed. Furthermore, identification of the pathological changes may provide insights into the pathogenic mechanisms, thereby facilitating development of a therapeutic strategy against neurodegenerative diseases.

In our previous report using molecular, biological, and immunocytochemical approaches, we uncovered that a pathway including p38-Akt-Bmi-1-p21 plays a critical role in the survival, self-renewal, and proliferation of NSCs (Kim and Wong, 2009a; Kim et al., 2011). We have shown that $Atm_{-/-}$ NSCs have elevated ROS levels with activation of p38, which is accompanied by Bmi-1 downregulation and p21 upregulation. However, inhibition of p38 activation results in upregulation of Bmi-1, which then restores self-renewal and proliferation of $Atm_{-/-}$ NSCs. These results indicate that Bmi-1 is essential for NSC survival, and that downregulation of Bmi-1 by p38 signaling may lead to growth arrest and defective self-renewal and proliferation of these cells. We demonstrated that a similar proportion of apoptotic nuclei and similar levels of cleaved caspase 3 and γ-H2AX were seen in $Atm_{+/+}$ and $Atm_{-/-}$ NSCs (Kim and Wong, 2009a). We concluded that depletion of NSCs in the $Atm_{-/-}$ mice may not be a result of apoptosis of NSCs.

Here we carried out in vivo studies focusing on alterations within the SVZ in $Atm_{-/-}$ mice. Our data indicated that depletion of NSCs in the SVZ is a prominent neuropathological feature in $Atm_{-/-}$ mice. We also revealed that the essential factors Bmi-1 and p21 observed previously during in vitro studies were altered in the $Atm_{-/-}$ SVZ, showing markedly lower levels of Bmi-1 and higher levels of p21 compared to $Atm_{+/+}$ SVZ (FIG. 1). Bmi-1, a component of the polycomb repressive complex, is necessary for normal NSC self-renewal and survival because it epigenetically silences genes that encode the cell cycle inhibitors p16, p19, and p21 (Molofsky et al., 2005, 2003; Leung et al., 2004; Fasano et al., 2007). Bmi-1 is also thought to inhibit aging through the suppression of p53 (Chatoo et al., 2009). Accordingly, shRNA knockdown of bmi-1 results in upregulation of p21, which in turn causes suppression of NSC self-renewal and proliferation (Leung et al., 2004). Bmi-1 deficient mice also exhibit postnatal depletion of NSCs that leads to neurological abnormalities and ataxia (Fasano et al., 2007). These results suggest that both ATM and Bmi-1 play similar roles in the process of NSC survival and proliferation. Compared to $Atm_{+/+}$ SVZ tissue, p38 signaling is constitutively activated in $Atm_{-/-}$ SVZ, which contributes to NSC depletion (FIG. 2). Normal p38 signaling is essential for neuronal differentiation (Androutsellis-Theotokis et al., 2006) and p38 activation resulted in abnormal differentiation in NPC1$_{-/-}$ (The Niemann-Pick type C1) NSCs (Yang et al., 2006). By contrast, p38 signaling is suppressed in proliferating NSCs (Lim et al., 2007). These observations support the idea that Atm$_{-/-}$ SVZ may be more enriched in the quiescent NSCs, which still maintain the ability to differentiate, albeit abnormally. Consistent with this idea, we also observed that Atm$_{-/-}$ NSCs in culture are capable of undergoing differentiation, but they have different frequencies of differentiated neuronal cells when compared to Atm$_{+/+}$ NSCs (FIG. 5A). Therefore, it is possible that the NSC status in Atm$_{-/-}$ SVZ represents the defective self-renewal and survival concomitant with increased and altered differentiation events.

Based on these observations, we examined whether inhibition of p38 signaling may reverse the impairment of NSC survival and neurogenesis to recover the neurological deficits in Atm$_{-/-}$ mice. We showed that a p38 specific inhibitor, SB203580, (4-[5-(4-Fluorophenyl)-2-[4-(methylsulphonyl)phenyl]-1H-imidazol-4-yl]pyridine) increased vimentin- and nestin-positive NSCs and restored Bmi-1 levels in Atm$_{-/-}$ SVZ (FIG. 3). The number of Purkinje cells in cerebellum was also increased in SB203580 (4-[5-(4-Fluorophenyl)-2-[4-(methylsulphonyl)phenyl]-1H-imidazol-4-yl]pyridine) treated Atm$_{-/-}$ cerebellum (FIG. 4). This is the first report in which a treatment targeting the p38 specific pathway in NSCs has been shown to restore degenerate neurons and correct neurological deficits in A-T. Our results substantiate our previous report that activation of p38 leads to defective self-renewal and survival through downregulation of Bmi-1 in cultured Atm$_{-/-}$ NSCs (Kim and Wong, 2009a; Kim et al., 2011). An interesting question that warrants further investigation is whether or not p38-dependent Bmi-1 phosphorylation is critical for the regulation of Bmi-1 levels. It is unclear from our study if Bmi-1 is a direct p38 substrate. Other studies have shown that Bmi-1 could be phosphorylated by 3pk (MAPKAP kinase 3), which is a downstream effector of p38 (Voncken et al., 2005).

Although this report shows abnormal SVZ in Atm$_{-/-}$ mice (FIG. 2), no significant differences in the number of vimentin-positive NSCs were observed in the hippocampus of Atm$_{+/+}$ and Atm$_{-/-}$ mice. Similar levels of Bmi-1 and p21 expression were also shown in the hippocampus tissue (data not shown). It is likely that Atm deficiency may not specifically affect hippocampal NSCs in the adult mice, although the reason for this difference is presently unclear. On the other hand, there was a significant increase in hippocampal GFAP-positive astrocyte cell number in 3-month-old Atm$_{-/-}$ mice and SB203580 (4-[5-(4-Fluorophenyl)-2-[4-(methylsulphonyl)phenyl]-1H-imidazol-4-yl]pyridine) treatment reduced astrocyte activation (data not shown). Consistent with previous reports (Eilam et al., 1998, 2003; Liu et al., 2005), the loss of dopaminergic neurons in both the striatum and the substantia nigra was accompanied by gliosis, a hallmark of the CNS inflammatory response (Chen and Swanson, 2003; Pekny and Nilsson, 2005; Reyes et al., 2008). It would be interesting to investigate in future studies whether SB203580 (4-[5-(4-Fluorophenyl)-2-[4-(methylsulphonyl)phenyl]-1H-imidazol-4-yl]pyridine) treatment also improves the number of dopaminergic neurons in hippocampus.

NSC transplantation has proven to be a more tractable therapeutic strategy for neurodegenerative disorders than the conventional replacement of differentiated neurons. Recent studies suggest that NSCs may hold promise for the therapeutic treatment of human genetic diseases resulting in neurodegeneration. For example, in the nervous (nr) mutant mice, PNs become abnormal and dysfunctional by the second postnatal week, and a majority of PNs die by the fifth week (Doulazmi et al., 2002; Seyfried et al., 1987). By transplanting normal NSCs into the cerebellum of nr mutant mice, PN function is repaired not just by cell replacement, but also by rectifying their gene expression and restoring defective molecular homeostasis due to the gene defect (Li et al., 2006a, 2006b). In another study, intracranial transplantation of normal NSCs was used to treat mice in a model of the human Sandhoff disease (Lee et al, 2007). This study shows that the transplantation of normal NSCs into diseased brains delays disease onset, preserves motor function, and prolongs survival of the diseased mice. These two studies show that NSCs may have a broad repertoire of therapeutic actions, of which neuronal replacement is but one. Since NSCs are defective in Atm$_{-/-}$ SVZ, transplanting normal Atm$_{+/+}$ NSCs may rescue impaired NSCs by restoring homeostasis to the NSCs themselves, or by stabilizing normal metabolism and redox balance in the supporting cell microenvironment. We have shown that NSCs in Atm$_{-/-}$ SVZ have abnormally reduced levels of Bmi-1, and we know from the work of other researchers that Bmi-1 is necessary for the improvement of NSC survival and proliferation (Molofsky et al., 2003, 2005). Transplantation of normal Atm$_{+/+}$ NSCs into Atm$_{-/-}$ mouse brains may thus promote a return to normal levels of Bmi-1 in the Atm$_{-/-}$ NSCs. In the next study, we would like to develop a reliable NSC transplantation protocol in order to determine whether Atm$_{+/+}$ NSC transplantation into SVZ of Atm$_{-/-}$ mice alters p38 signaling of Atm$_{-/-}$ SVZ tissue and leads to functional recovery of Atm$_{-/-}$ mice.

In conclusion, this study showed that Atm$_{-/-}$ SVZ has intrinsic impairments in NSC survival that may lead to abnormal differentiation and composition of neuronal cells in various areas of the brain, such as the cerebellum and substantia nigra. Our study also revealed that it is possible to functionally enrich NSCs that reside within the SVZ using a p38 inhibitor with beneficial consequence in the cytoarchitecture in the cerebellum of the Atm$_{-/-}$ mice. Based on our observations, we believe that controlling NSC survival may be therapeutically useful in the treatment of A-T neurodegeneration. Our research provides for the implementation of our previous findings and may hold possible chemical treatments combined with stem cell therapy that will help those in need of brain cell replacement.

REFERENCES

Allen D M, van Praag H, Ray J, Weaver Z, Winrow C J, Carter T A, Braquet R, Harrington E, Ried T, Brown K D, Gage F H, Barlow C (2001) Ataxia telangiectasia mutated is essential during adult neurogenesis. *Genes Dev* 15:554-566.

Androutsellis-Theotokis A, Leker R R, Soldner F, Hoeppner D J, Ravin R, Poser S W, Rueger M A, Bae S K, Kittappa R, McKay R D (2006) Notch signaling regulates stem cell numbers in vitro and in vivo. *Nature* 442:823-826.

Barlow C, Hirotsune S, Paylor R, Liyanage M, Eckhaus M, Collins F, Shiloh Y, Crawley J N, Ried T, Tagle D, Wynshaw-Boris A (1996) Atm-Deficient Mice: A Paradigm of Ataxia Telangiectasia. *Cell* 86: 159-171.

Boder E (1985) Ataxia-telangiectasia: an overview. In *Kroc Foundation Series* (Gatti R A and Swift M, eds) 19:1-63. Alan R. Liss, New York.

Boder E, Sedgwick R P (1958) Ataxia-telangiectasia; a familial syndrome of progressive cerebellar ataxia, oculocutaneous telangiectasia and frequent pulmonary infection. *Pediatrics* 21:526-554.

Browne S E, Roberts U 2nd, Dennery P A, Doctrow S R, Beal M F, Barlow C, Levine R L (2004) Treatment with a catalytic antioxidant corrects the neurobehavioral defect in ataxia-telangiectasia mice. *Free Radic Biol Med* 36:938-942.

Chatoo W, Abdouh M, David J, Champagne M P, Ferreira J, Rodier F, Bernier G (2009) The polycomb group gene Bmi1 regulates antioxidant defenses in neurons by repressing p53 pro-oxidant activity. *J Neurosci* 29:529-542.

Chen Y, Swanson R A (2003) Astrocytes and brain injury. *J Cereb Blood Flow Metab* 23:137-149.

Curtis M A, Faull R L, Eriksson P S (2007) The effect of neurodegenerative diseases on the subventricular zone. *Nat Rev Neurosci* 8:712-723.

Doulazmi M, Hadj-Sahraoui N, Frederic F, Mariani J (2002) Diminishing Purkinje cell populations in the cerebella of aging heterozygous Purkinje cell degeneration but not heterozygous nervous mice. *J Neurogenet* 16:111-123.

Eilam R, Peter Y, Elson A, Rotman G, Shiloh Y, Groner Y, Segal M (1998) Selective loss of dopaminergic nigrostriatal neurons in brains of Atm-deficient mice. *Proc Natl Acad Sci USA* 95:12653-12656.

Eilam R, Peter Y, Groner Y, Segal M (2003) Late degeneration of nigrostriatal neurons in ATM-/- mice. *Neuroscience* 121:83-98.

Fasano C A, Dimos J T, Ivanova N B, Lowry N, Lemischka I R, Temple S (2007) shRNA knockdown of Bmi-1 reveals a critical role for p21-Rb pathway in NSC selfrenewal during development. *Cell Stem Cell* 1:87-99.

Fasano C A, Phoenix T N, Kokovay E, Lowry N, Elkabetz Y, Dimos J T, Lemischka I R, Studer L, Temple S (2009) Bmi-1 cooperates with Foxg1 to maintain neural stem cell self-renewal in the forebrain. *Genes Dev* 23:561-574.

Flax J D, Aurora S, Yang C, Simonin C, Wills A M, Billinghurst L L, Jendoubi M, Sidman R L, Wolfe J H, Kim S U, Snyder E Y (1998) Engraftable human neural stem cells respond to developmental cues, replace neurons, and express foreign genes. *Nat Biotechnol* 16:1033-1039.

Gage F H (2000) Mammalian Neural Stem Cells. *Science* 287:1433-1438.

Gueven N, Luff J, Peng C, Hosokawa K, Bottle S E, Lavin M F (2006) Dramatic extension of tumor latency and correction of neurobehavioral phenotype in Atm-mutant mice with a nitroxide antioxidant. *Free Radic Biol Med* 41:992-1000.

Kim J, Hwangbo J, and Wong P K (2011) p38 MAPK-Mediated Bmi-1 Down-Regulation and Defective Proliferation in ATM-Deficient Neural Stem Cells Can Be Restored by Akt Activation. *PLoS ONE* 6:e16615.

Kim J, Wong P K (2009a) Loss of ATM Impairs Proliferation of Neural Stem Cells Through Oxidative Stress-Mediated p38 MAPK Signaling. *Stem Cells* 27:1987-1998.

Kim J, Wong P K (2009b) Oxidative stress is linked to ERK1/2-p16 signaling-mediated growth defect in ATM-deficient astrocytes. *J Biol Chem* 284:14396-14404.

Kuljis R O, Xu Y, Aguila M C, Baltimore D (1997) Degeneration of neurons, synapses, and neuropil and glial activation in a murine $Atm_{-/-}$ model of ataxia-telangiectasia. *Proc Natl Acad Sci USA* 94:12688-12693.

Lee J P, Jeyakumar M, Gonzalez R, Takahashi H, Lee P J, Baek R C, Clark D, Rose H, Fu G, Clarke J, McKercher S, Meerloo J, Muller F J, Park K I, Butters T D, Dwek R A, Schwartz P, Tong G, Wenger D, Lipton S A, Seyfried T N, Platt F M, Snyder E Y (2007) Stem cells act through multiple mechanisms to benefit mice with neurodegenerative metabolic disease. *Nat Med* 13:439-447.

Leung C, Lingbeek M, Shakhova O, Liu J, Tanger E, Saremaslani P, Van Lohuizen M, Marino S (2004) Bmi1 is essential for cerebellar development and is overexpressed in human medulloblastomas. *Nature* 428:337-341.

Li J, Imitola J, Snyder E Y, Sidman R L (2006a) Neural stem cells rescue nervous purkinje neurons by restoring molecular homeostasis of tissue plasminogen activator and downstream targets. *J Neurosci* 26:7839-7848.

Li J, Ma Y, Teng Y D, Zheng K, Vartanian T K, Snyder E Y, Sidman R L (2006b) Purkinje neuron degeneration in nervous (nr) mutant mice is mediated by a metabolic pathway involving excess tissue plasminogen activator. *Proc Natl Acad Sci USA* 103:7847-7852.

Lim M S, Nam S H, Kim S J, Kang S Y, Lee Y S, Kang K S (2007) Signaling pathways of the early differentiation of neural stem cells by neurotrophin-3. *Biochem Biophys Res Commun* 357:903-909.

Liu N, Stoica G, Yan M, Scofield V L, Qiang W, Lynn W S, Wong P K (2005) ATM deficiency induces oxidative stress and endoplasmic reticulum stress in astrocytes. *Lab Invest* 85:1471-1480.

Molofsky A V, He S, Bydon M, Morrison S J, Pardal R (2005) Bmi-1 promotes neural stem cell self-renewal and neural development but not mouse growth and survival by repressing the p16Ink4a and p19Arf senescence pathways. *Genes Dev* 19:1432-1437.

Molofsky A V, Pardal R, Iwashita T, Park I K, Clarke M F, Morrison S J (2003) Bmi-1 dependence distinguishes neural stem cell self-renewal from progenitor proliferation. *Nature* 425:962-967.

Oizumi H, Hayashita-Kinoh H, Hayakawa H, Arai H, Furuya T, Ren Y R, Yasuda T, Seki T, Mizuno Y, Mochizuki H (2008) Alteration in the differentiation-related molecular expression in the subventricular zone in a mouse model of Parkinson's disease. *Neurosci Res* 60:15-21.

Pekny M, Nilsson M (2005) Astrocyte activation and reactive gliosis. *Glia* 50:427-434.

Quinones-Hinojosa A, Chaichana K (2007) The human subventricular zone: A source of new cells and a potential source of brain tumors. *Exp Neurol* 205:313-324.

Reyes J F, Reynolds M R, Horowitz P M, Fu Y, Guillozet-Bongaarts A L, Berry R, Binder L I (2008) A possible link between astrocyte activation and tau nitration in Alzheimer's disease. *Neurobiol Dis* 31:198-208.

Sardanelli F, Parodi R C, Ottonello C, Renzetti P, Saitta S, Lignana E, Mancardi G L (1995) Cranial MRI in ataxia-telangiectasia. *Neuroradiology* 37:77-82.

Seyfried T N, Bernard D J, Yu R K (1987) Effect of Purkinje cell loss on cerebellar gangliosides in nervous mutant mice. *J Neurosci Res* 17:251-255.

Voncken J W, Niessen H, Neufels B, Rennefahrt U, Dahlmans V, Kubben N, Holzer B, Ludwig S, Rapp U R (2005) MAPKAP kinase 3pK phosphorylates and regulates chromatin association of the polycomb group protein Bmi1. *J Biol Chem* 280:5178-5187.

Yang S R, Kim S J, Byun K H, Hutchinson B, Lee B H, Michikawa M, Lee Y S, Kang K S (2006) NPC1 gene deficiency leads to lack of neural stem cell self-renewal and abnormal differentiation through activation of p38 mitogen-activated protein kinase signaling. *Stem Cells* 24:292-298.

A, Cytoarchitecture and NSC marker expression in adult (P90) $Atm_{+/+}$ and $Atm_{-/-}$ mice SVZ. Paraformaldehyde-fixed frozen sections of SVZ tissue were stained with H&E and antibody against vimentin. Representative images show that the NSC number was markedly reduced in the SVZ of $Atm_{-/-}$ mice. 8, SVZ sections of adult (P90) $Atm_{+/+}$ and $Atm_{-/-}$ mice were stained with antibodies against Bmi-1 and p21. Immunostaining shows alterations in levels of these molecules in the SVZ of $Atm_{-/-}$ mice. C, SVZ sections of adult (P90) $Atm_{+/+}$ and $Atm_{-/-}$ mice were stained with antibody against nestin (displayed as green) to identify NSCs. Cells were counterstained by DAPI (4'-6-Diamidino-2-phenylindole), which identifies the nuclei of the NSCs. NSCs were significantly reduced by >90% loss in the SVZ of $Atm_{-/-}$ mice. Scale bars: 50 μm (A), 50 μm (8) and 20 μm (C).

Figure 1:
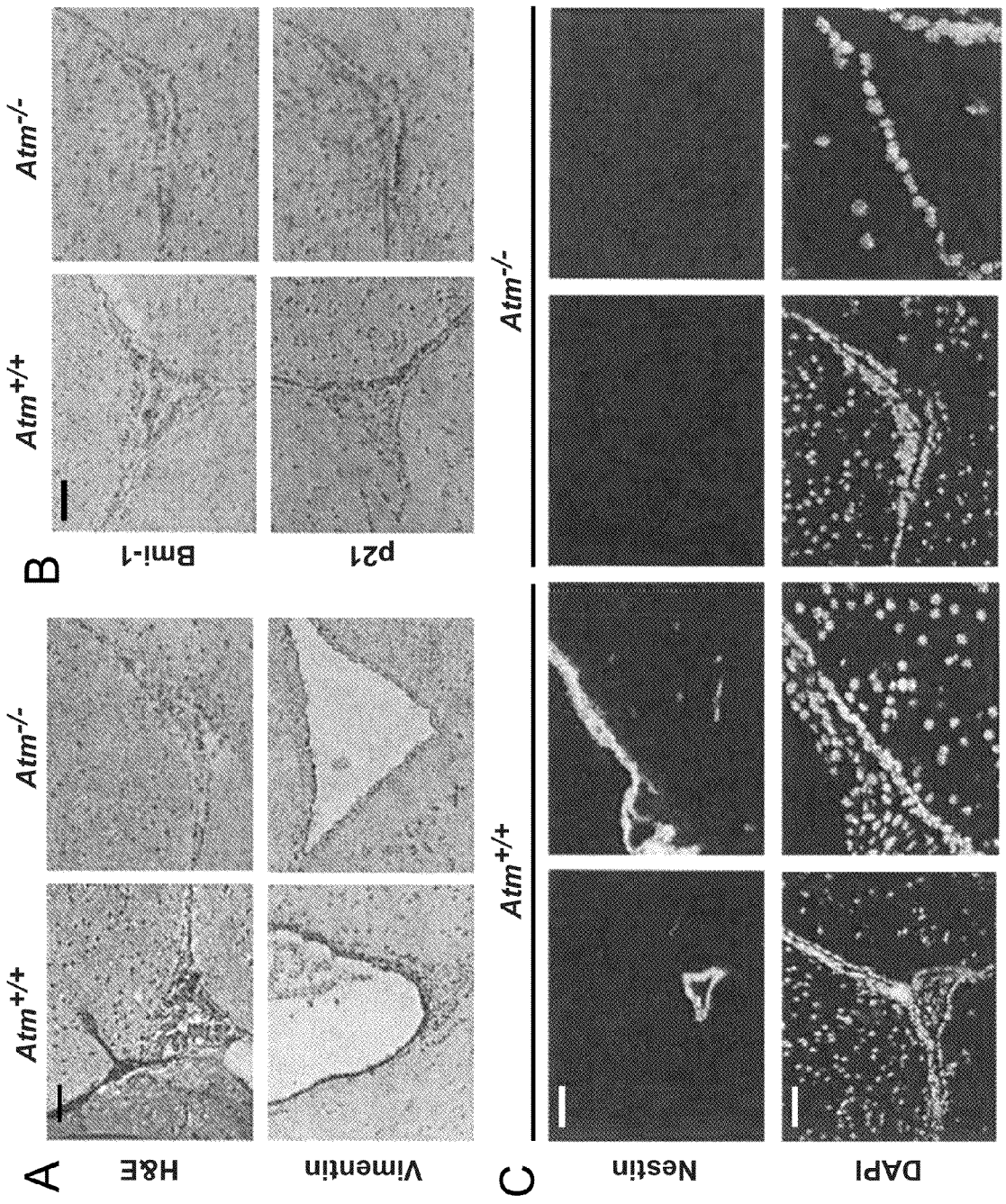
FIG. 1. Alterations in SVZ tissue of $Atm_{-/-}$ mice
Figure 2:
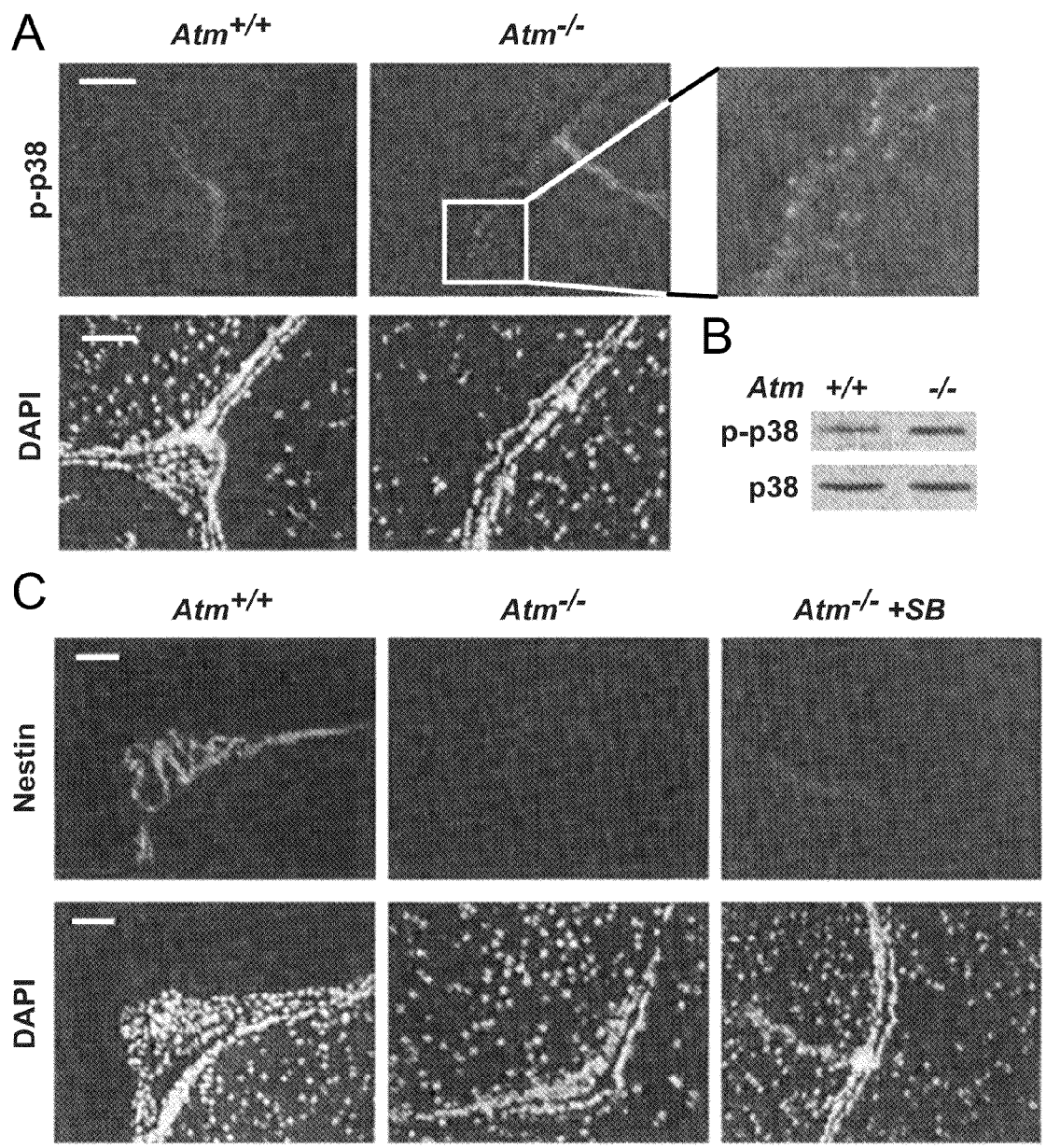

FIG. 2. p38 activation was responsible for NSC depletion in $Atm_{-/-}$ SVZ

A, Paraformaldehyde-fixed frozen sections of SVZ tissue of adult (P90) $Atm_{+/+}$ and $Atm_{-/-}$ mice were stained with antibody against phospho-p38 (p-p38; displayed as green). Cells were counterstained by DAPI. The right panel is an enlargement of the small grey frame in the left panel, showing p38 activation in SVZ tissue of $Atm_{-/-}$ mice. 8, Proteins were extracted from SVZ tissue of adult (P90) $Atm_{+/+}$ and $Atm_{-/-}$ mice. Western blot analysis confirmed elevated levels of phospho-p38 in $Atm_{-/-}$ SVZ tissue. C, 1 month-old $Atm_{+/+}$ and $Atm_{-/-}$ mice were either treated with PBS or SB203580 (4-[5-(4-Fluorophenyl)-2-[4-(methylsulphonyl)phenyl]-1H-imidazol-4-yl]pyridine) for 2 months. $Atm_{+/+}$, PBS-treated $Atm_{+/+}$ mice (n=10); $Atm_{-/-}$, PBS-treated $Atm_{-/-}$ mice (n=9); and $Atm_{-/-}$+SB, SB203580 (4-[5-(4-Fluorophenyl)-2-[4-(methylsulphonyl)phenyl]-1H-imidazol-4-yl]pyridine) treated $Atm_{-/-}$ mice (n=10). SVZ sections were stained with antibodies against nestin (displayed as red) for NSCs. Cells were counterstained by DAPI. Immunostaining results showed that nestin-positive NSCs are obviously depleted in SVZ tissue of $Atm_{-/-}$ mouse, but SB203580 (4-[5-(4-Fluorophenyl)-2-[4-(methylsulphonyl)phenyl]-1H-imidazol-4-yl]pyridine) partially restored NSCs. Scale bars: 20 μm (A) and 50 μm (C).

Figure 3A:
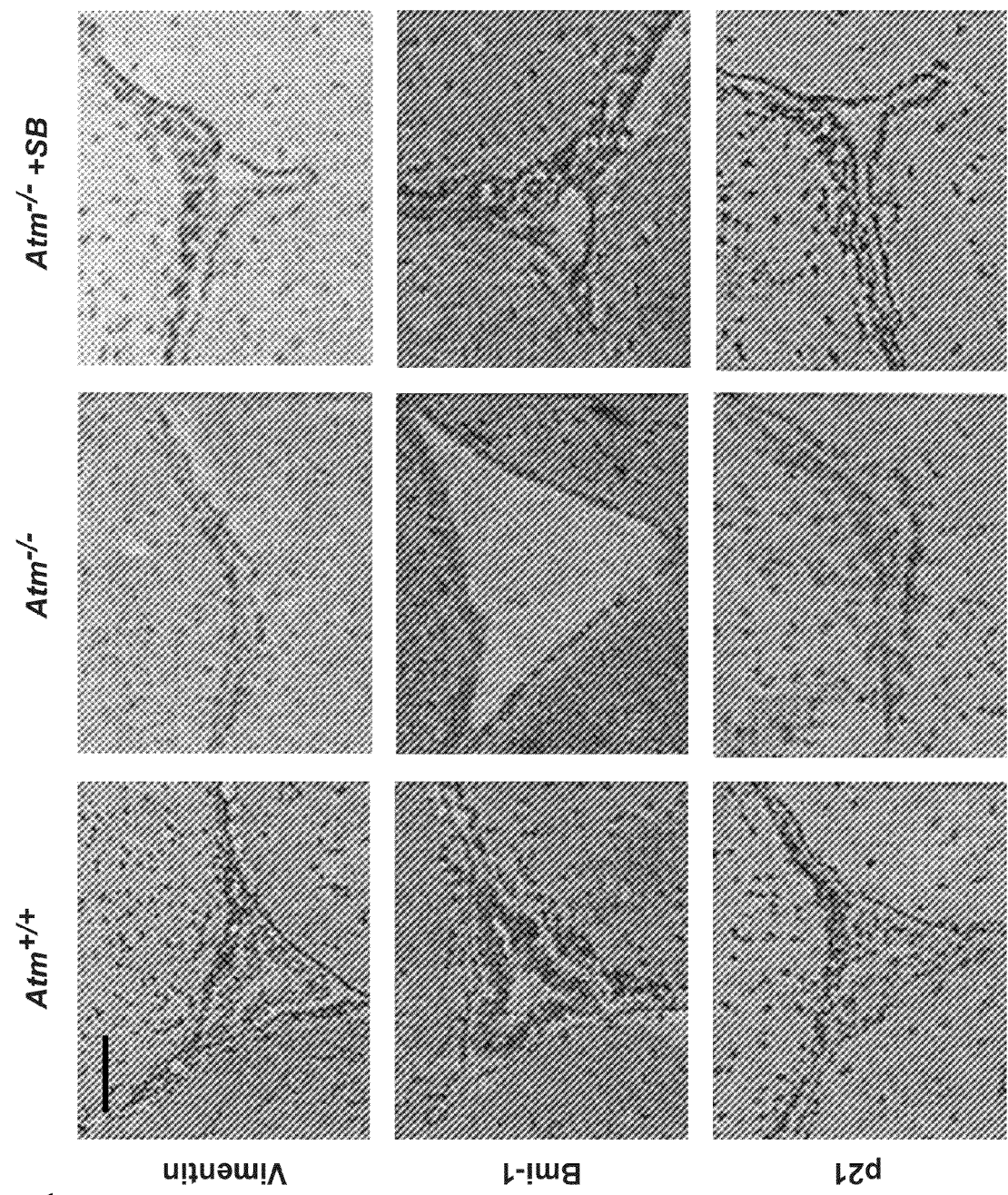
Figure 3D:
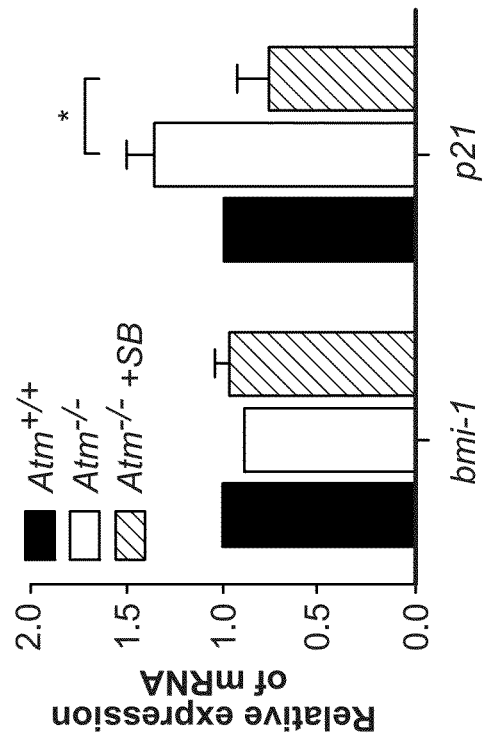
Figure 3C:
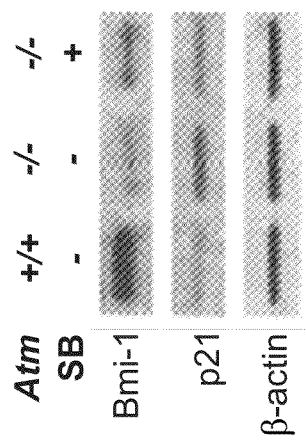

FIG. 3. Inactivation of p38 rescued NSCs of $Atm_{-/-}$ SVZ

A, 1 month-old $Atm_{+/+}$ and $Atm_{-/-}$ mice were treated with either PBS or SB203580 (4-[5-(4-Fluorophenyl)-2-[4-(methylsulphonyl)phenyl]-1H-imidazol-4-yl]pyridine) for 2 months. After treatments, SVZ sections of $Atm_{+/+}$, $Atm_{-/-}$, and $Atm_{-/-}$+SB mice were stained with antibodies against vimentin, Bmi-1 and p21. Immunostaining images showed that levels of signaling molecules altered in $Atm_{-/-}$ SVZ, but SB203580 (4-[5-(4-Fluorophenyl)-2-[4-(methylsulphonyl)phenyl]-1H-imidazol-4-yl]pyridine) restored these alterations to normal. B, Immunostaining of SVZ sections with anti-Bmi1 antibody (displayed as green) revealed that Bmi-1 level is restored by SB203580 (4-[5-(4-Fluorophenyl)-2-[4-(methylsulphonyl)phenyl]-1H-imidazol-4-yl]pyridine) treatment in SVZ of $Atm_{-/-}$ mouse. C, Western blot analysis further confirmed that levels of Bmi-1 and p21 were restored by SB203580 (4-[5-(4-Fluorophenyl)-2-[4-(methylsulphonyl)phenyl]-1H-imidazol-4-yl]pyridine) treatment in SVZ tissue of $Atm_{-/-}$ mice. D, Total RNA was purified from SVZ tissues of adult (P90) $Atm_{+/+}$, $Atm_{-/-}$, and $Atm_{-/-}$+SB mice and analyzed by quantitative RT-PCR for bmi-1 and p21 expression. Probing for gapdh was used as an internal control. Scale bars: 20 μm (A) and (8). SB, SB203580 (4-[5-(4-Fluorophenyl)-2-[4-(methylsulphonyl)phenyl]-1H-imidazol-4-yl]pyridine).

Figure 4:
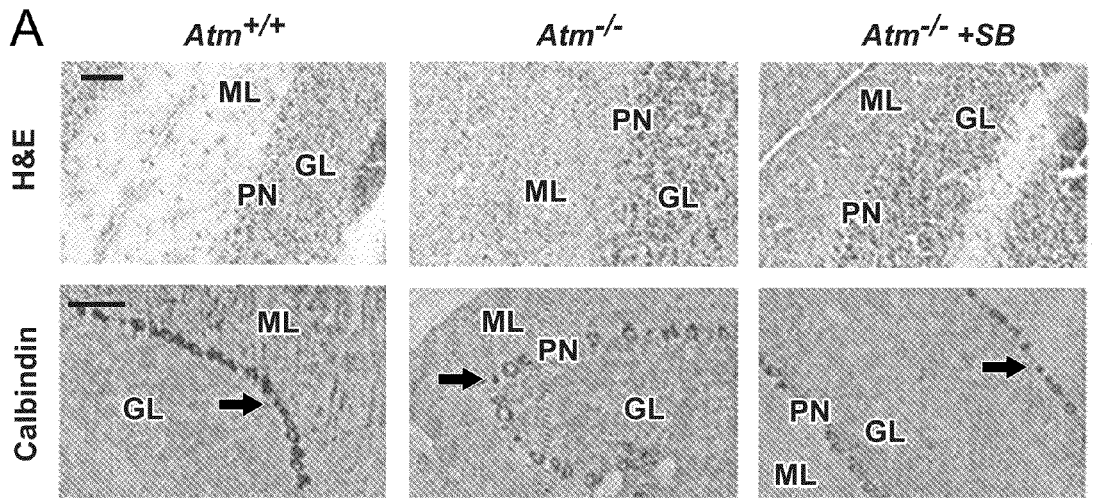
Figure 4:
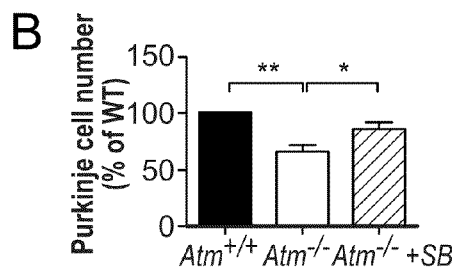
Figure 4:
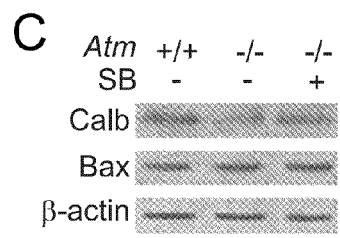
Figure 4:
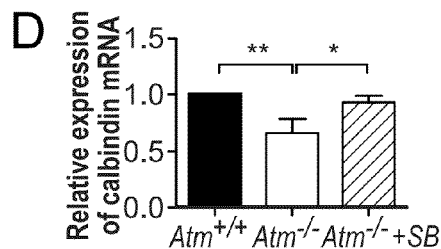
Figure 4:
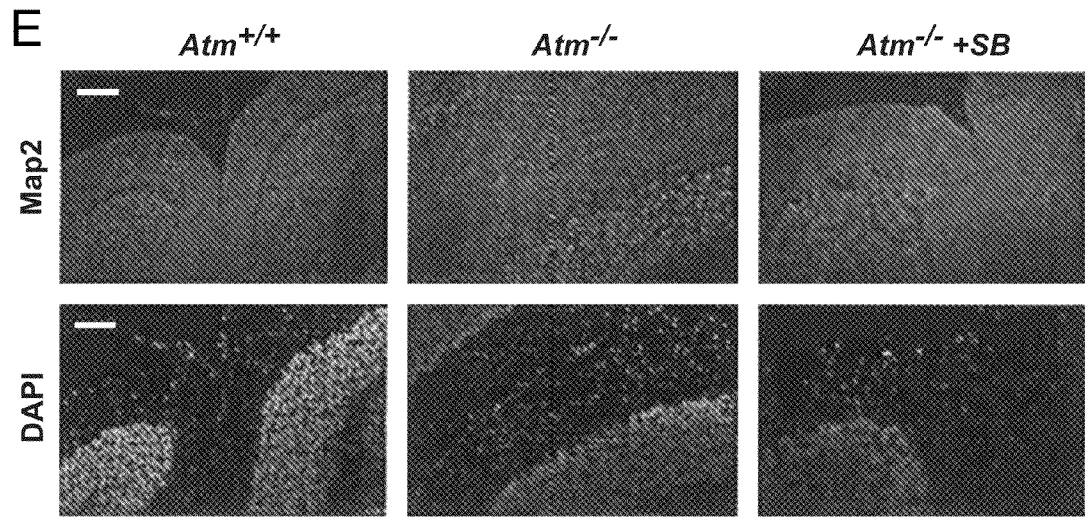

FIG. 4. SB2203580 protected $Atm_{-/-}$ cerebellar Purkinje cells

A, 1 month-old $Atm_{+/+}$ and $Atm_{-/-}$ mice were either treated with PBS or SB203580 (4-5-(4-Fluorophenyl)-2-[4-(methylsulphonyl)phenyl]-1H-imidazol-4-yl]pyridine) for 2 months, and then cytoarchitecture and neuronal marker expression of adult (P90) $Atm_{+/+}$, $Atm_{-/-}$, and $Atm_{-/-}$+SB mice cerebellum were investigated. Upper panel, H&Estained section of cerebellum displays cytoarchitecture, including the external GL, the PN, and the ML layer (GL, granular layer; PN, Purkinje neuron layer; ML, molecular layer). Lower panel, paraformaldehyde-fixed frozen sections of cerebellar tissue of adult (P90) $Atm_{+/+}$, $Atm_{-/-}$, and $Atm_{-/-}$+SB mice were stained with antibody against calb for Purkinje cells. Arrows point to degenerated Purkinje cell bodies. Immunostaining images showed that the Purkinje cell number was reduced in the cerebellar hemispheres of $Atm_{-/-}$ mice and was preserved by SB203580 (4-[5-(4-Fluorophenyl)-2-[4-(methylsulphonyl)phenyl]-1H-imidazol-4-yl]pyridine) treatment. B, Purkinje cell numbers in cerebellar hemispheres of adult (P90) $Atm_{+/+}$, $Atm_{-/-}$, and $Atm_{-/-}$+SB mice. Values represent percentage of $Atm_{+/+}$ Purkinje cell number±SD (Three independent counting of 10 fields; *, P<0.05). C, Western blot analysis with antibody against calb further confirmed that reduction of calb protein is rescued by SB203580 (4-[5-(4-Fluorophenyl)-2-[4-(methylsulphonyl)phenyl]-1H-imidazol-4-yl]pyridine) in cerebellar tissue of $Atm_{-/-}$ mice. No change was found in levels of Bax. D, Expression of calbindin mRNA detected by qRTPCR was downregulated in adult (P90) $Atm_{-/-}$ mice cerebellum but was restored by SB203580 (4-[5-(4-Fluorophenyl)-2-[4-(methylsulphonyl)phenyl]-1H-imidazol-4-yl]pyridine). Probing for gapdh was used as an internal control (**, P<0.01, *, P<0.05). E, Cerebellar sections of adult (P90) $Atm_{+/+}$, $Atm_{-/-}$, and $Atm_{-/-}$+SB mice were stained with anti-Map2 antibody for dendritic networks. Map2 immunoreactivity showed that although cerebella from $Atm_{-/-}$ mice showed reduced calb-positive Purkinje cells in the PN and in the ML, they had an extensive dendritic network (Map2-positive structure) both in $Atm_{+/+}$ and $Atm_{-/-}$ mice. Scale bars: 500 μm (A, upper panel), 50 μm (A, lower panel) and (E). SB, SB203580 (4-[5-(4-Fluorophenyl)-2-[4-(methylsulphonyl)phenyl]-1H-imidazol-4-yl]pyridine).

Figure 5:
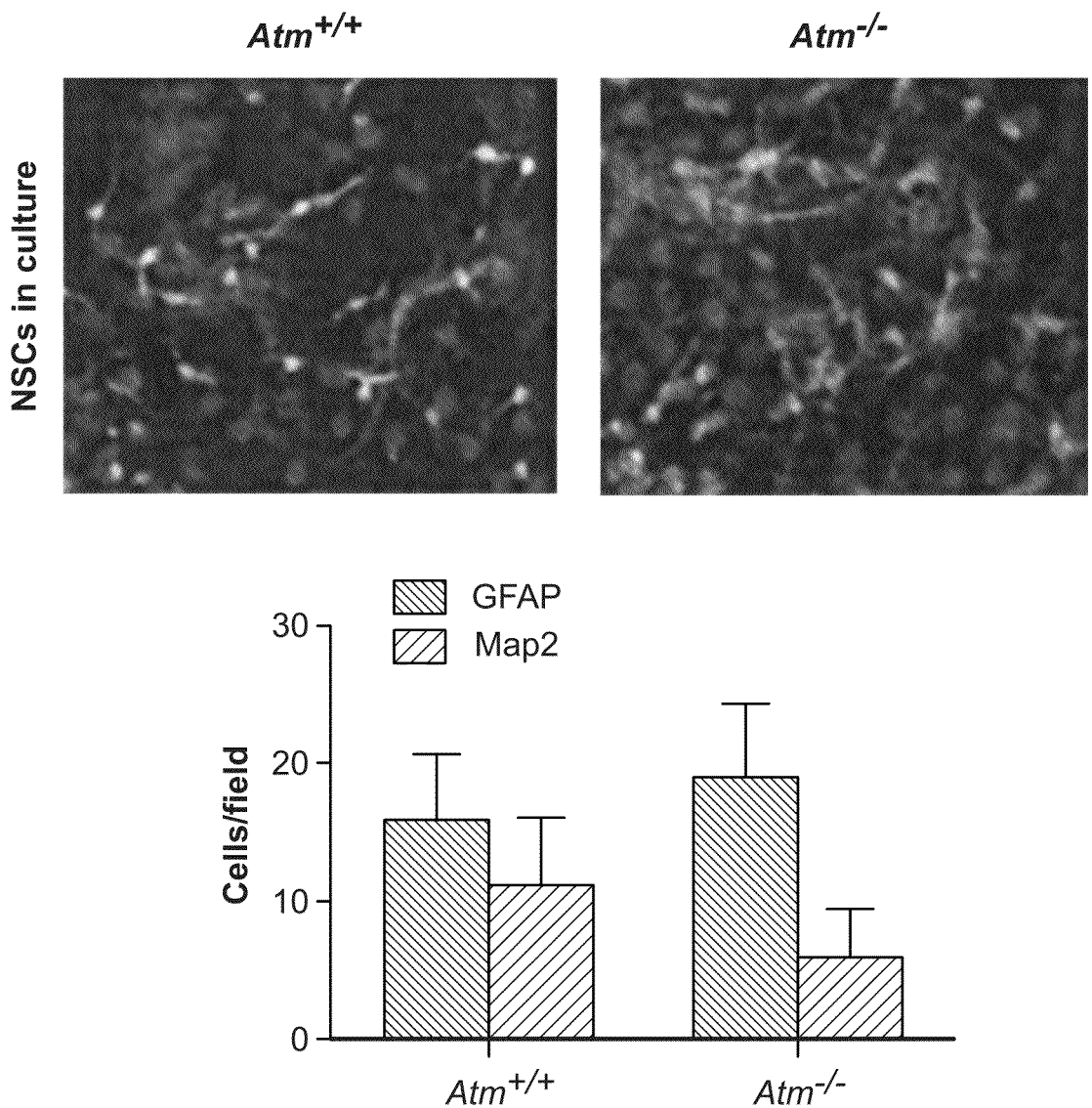

FIG. 5. Loss of ATM resulted in abnormal differentiation in $Atm_{-/-}$ NSCs

To induce $Atm_{+/+}$ and $Atm_{-/-}$ NSCs to differentiate, cells were incubated in medium containing 10% FBS for 7 days without EGF, and then differentiated cells were stained with antibodies against GFAP and Map2 to detect astrocytes and neurons, respectively. Representative images showed abnormal differentiation patterns in $Atm_{-/-}$ NSCs. Compositions of differentiated neuronal cells were different between $Atm_{+/+}$ and $Atm_{-/-}$ NSCs in culture. Values represent the number of astrocytes and neurons in a field±SD (15 fields were taken from $Atm_{+/+}$ and $Atm_{-/-}$ NSCs).

Figure 6:
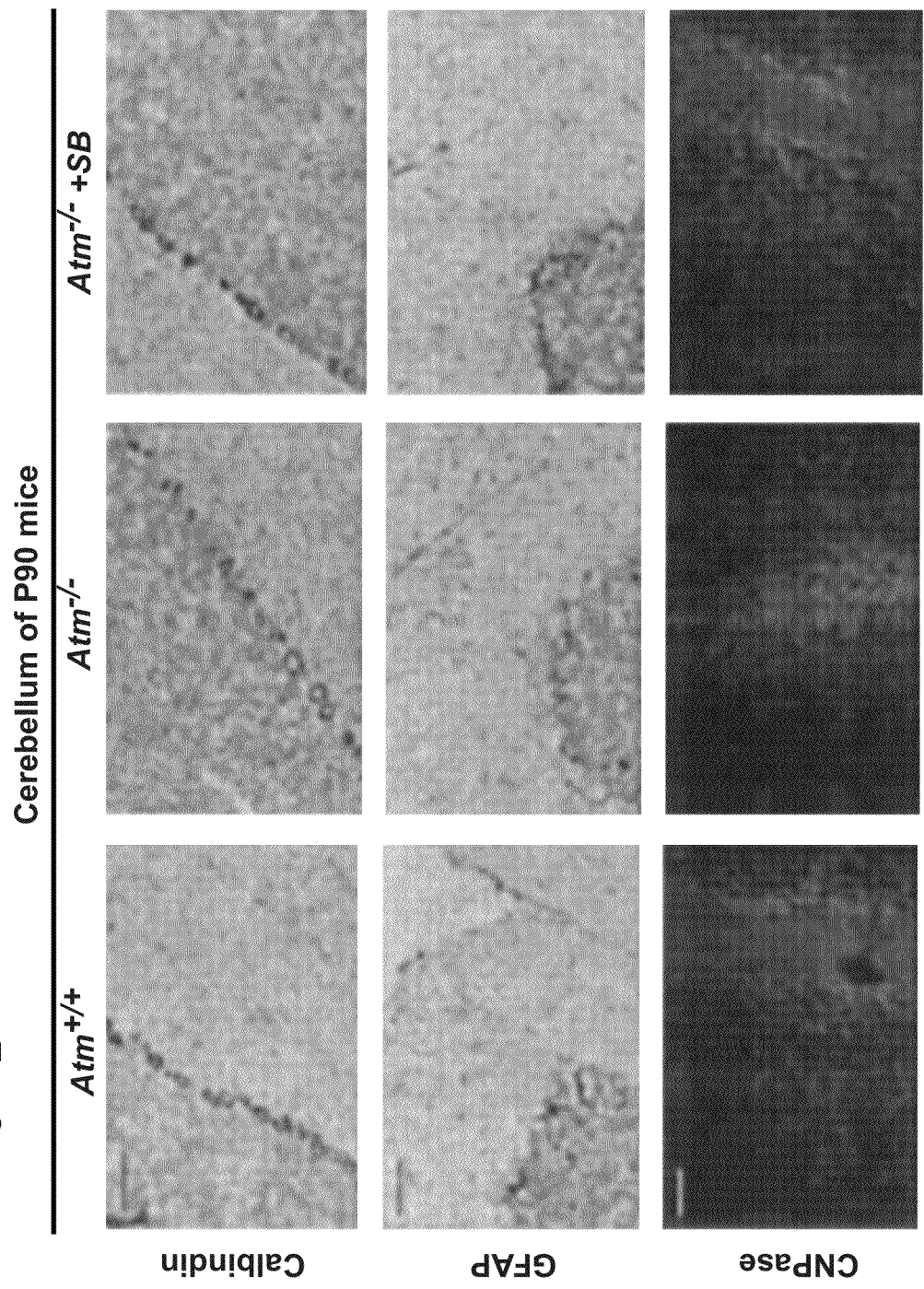

FIG. 6. The effects of SB203580 treatment on neurogenesis in $Atm_{-/-}$ mice

Cerebellar sections of adult (P90) $Atm_{+/+}$, $Atm_{-/-}$, and $Atm_{-/-}$+SB mice were stained with antibodies against calb for Purkinje cells, GFAP for astrocytes, and CNPase (displayed as red) for oligodendrocytes. Representative immunostaining images showed that SB203580 (4-[5-(4-Fluorophenyl)-2-[4-(methylsulphonyl)phenyl]-1H-imidazol-4-yl] pyridine) treatment led to normal NSC differentiation in $Atm_{-/-}$ mice. Scale bars: 50 μm. SB, SB203580 (4-[5-(4-Fluorophenyl)-2-[4-(methylsulphonyl)phenyl]-1H-imidazol-4-yl]pyridine).

Figure 7:
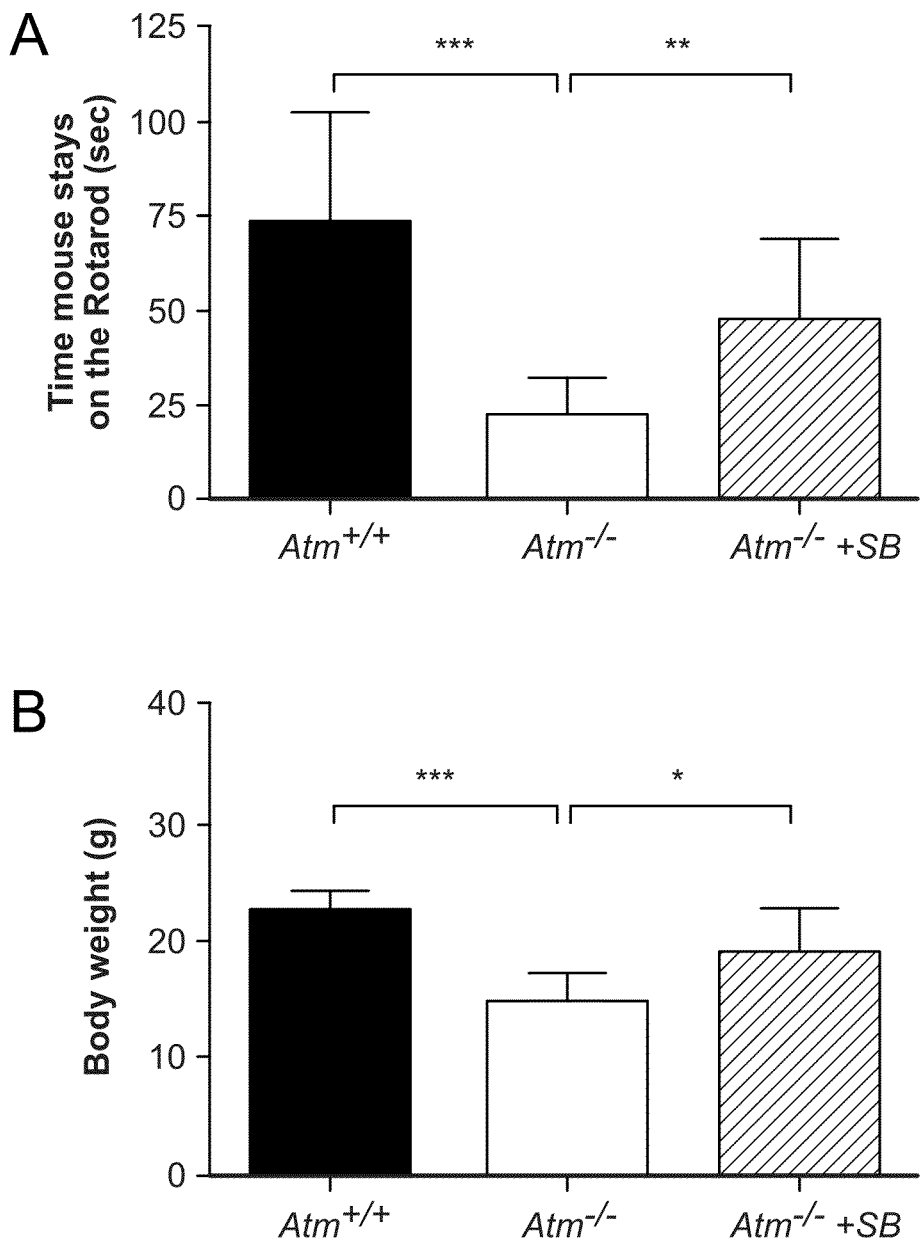

FIG. 7. SB203580 retained their motor function of $Atm_{-/-}$ mice

A, After SB203580 (4-[5-(4-Fluorophenyl)-2-[4-(methylsulphonyl)phenyl]-1H-imidazol-4-yl]pyridine) treatment, motor coordination of adult (P90) $Atm_{+/+}$, $Atm_{-/-}$, and $Atm_{-/-}$+SB mice was assessed by measuring the time before falling off the rotarod at 25 rpm with three trials. Values represent means±SD of time on the rotating rod ($Atm_{+/+}$, n=10; $Atm_{-/-}$, n=9; $Atm_{-/-}$+SB, n=10. Three independent tests; *, P<0.001, , P<0.01). Results of the rotarod test showed that SB203580 (4-[5-(4-Fluorophenyl)-2-[4-(methylsulphonyl)phenyl]-1H-imidazol-4-yl]pyridine) treatment significantly restored the motor function of $Atm_{-/-}$ mice. B, After SB203580 (4-[5-(4-Fluorophenyl)-2-[4-(methylsulphonyl)phenyl]-1H-imidazol-4-yl]pyridine) treatment, body weight of adult (P90) $Atm_{+/+}$, $Atm_{-/-}$, and $Atm_{-/-}$+SB mice was measured. Values represent means±SD of bodyweight ($Atm_{+/+}$, n=10; $Atm_{-/-}$, n=9; $Atm_{-/-}$+SB, n=10. Three independent tests; ***, P<0.001, *, P<0.05). Results showed that SB203580 treatment did not harm $Atm_{+/+}$ mice but significantly increased body weight of $Atm_{-/-}$ mice. SB, SB203580 (4-[5-(4-Fluorophenyl)-2-[4-(methylsulphonyl)phenyl]-1H-imidazol-4-yl]pyridine).

The invention claimed is:

1. A method for treating ataxia-telangiectasis (A-T) in a subject in need thereof comprising administering 4-[5-(4-Fluorophenyl)-2-[4-(methylsulphonyl)phenyl]-1H-imidazol-4-yl]pyridine.

* * * * *